US008954150B2

(12) United States Patent
Swanson et al.

(10) Patent No.: US 8,954,150 B2
(45) Date of Patent: Feb. 10, 2015

(54) SIDE MOUNT FEEDTHROUGH SYSTEM FOR SEALED COMPONENTS

(75) Inventors: Lawrence D. Swanson, White Bear Lake, MN (US); John M. Edgell, Plymouth, MN (US); Nick A. Youker, River Falls, WI (US); John E. Hansen, Ham Lake, MN (US); David A. Chizek, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 597 days.

(21) Appl. No.: 12/878,406

(22) Filed: Sep. 9, 2010

(65) Prior Publication Data

US 2011/0082531 A1     Apr. 7, 2011

Related U.S. Application Data

(60) Provisional application No. 61/248,682, filed on Oct. 5, 2009.

(51) Int. Cl.
*A61N 1/372* (2006.01)
*A61N 1/375* (2006.01)

(52) U.S. Cl.
CPC .................................... *A61N 1/3754* (2013.01)
USPC .......................................................... 607/36

(58) Field of Classification Search
CPC ................................................... A61N 1/3758

USPC ............................................................ 607/36
See application file for complete search history.

(56) References Cited

U.S. PATENT DOCUMENTS

| 6,026,325 | A | 2/2000 | Weinberg et al. |
| 6,721,602 | B2* | 4/2004 | Engmark et al. ................ 607/36 |
| 6,881,516 | B2* | 4/2005 | Aamodt et al. ............... 429/181 |
| 6,888,715 | B2 | 5/2005 | Stevenson et al. |
| 6,984,145 | B1 | 1/2006 | Lim |
| 7,211,884 | B1 | 5/2007 | Davis et al. |
| 7,214,068 | B2* | 5/2007 | Kronich et al. ................. 439/65 |
| 7,511,938 | B2 | 3/2009 | Elam et al. |
| 7,623,335 | B2 | 11/2009 | Stevenson et al. |
| 7,803,014 | B2* | 9/2010 | Sprain et al. .................. 439/526 |
| 2002/0116035 | A1 | 8/2002 | Klehn |
| 2003/0192171 | A1 | 10/2003 | Fey et al. |
| 2006/0107506 | A1 | 5/2006 | Doffing et al. |

* cited by examiner

*Primary Examiner* — Luther Behringer
(74) *Attorney, Agent, or Firm* — Schwegman Lundberg & Woessner, P.A.

(57) ABSTRACT

The present subject matter provides apparatus and methods for manufacturing an encasement for a component of an implantable medical device having a main circuit board. The method includes forming an encasement aperture on a lateral side of the encasement. The lateral side of the encasement is adapted to be placed substantially parallel to a surface of the main circuit board. A feedthrough assembly is connected through the encasement aperture. The feedthrough assembly includes at least one terminal conductor at least partially passing through the encasement aperture.

20 Claims, 6 Drawing Sheets

SIDE MOUNT FEEDTHROUGH SYSTEM FOR SEALED COMPONENTS

CLAIM OF PRIORITY

This application claims the benefit of provisional U.S. patent application Ser. No. 61/248,682, filed on Oct. 5, 2009, which is hereby incorporated by reference in its entirety.

TECHNICAL FIELD

This application relates generally to electrical feedthrough assemblies for use in implantable medical devices, and more particularly, to side mount feedthrough assemblies for sealed components of implantable medical devices.

BACKGROUND

Numerous applications involve penetrating a sealed encasement (i.e., a container) so-as-to provide electrical access to or from electrical components enclosed within. One such application involves body implantable medical devices (referred to as "IMDs"), such as pulse generators or cardiac function management devices, for the treatment of bradycardia, tachyarrhythmia, or muscle or nerve stimulation. One such example involves providing electrical access to and from a power source (e.g., a battery) of an IMD.

Electrical feedthrough assemblies provide a conductive path extending between the interior of the hermetically sealed encasement and a location outside the encasement. Typically, the conductive path comprises a conductive pin or other type of terminal that is electrically insulated from the encasement. In addition, feedthrough assemblies may include a ferrule and an insulative material for positioning and insulating the pin within the ferrule. In the battery power source example, a conductive connection member is often directly coupled to an internal portion (i.e., a portion located within the battery encasement) of the conductive pin on a first end and coupled to an anode or cathode of the battery on a second end.

When used in IMDs, feedthrough assemblies need to provide years of reliable service as they are difficult to repair.

SUMMARY

Various embodiments disclosed herein provide feedthrough assemblies that comprise, among other things, highly reliable components and secure interconnections. The present subject matter provides encasements for components of implantable medical devices and methods for their manufacture. An encasement for a component of an implantable medical device having a main circuit board includes an encasement aperture on a lateral side of the encasement. The lateral side of the encasement is adapted to be placed substantially parallel to a surface of the main circuit board. The encasement further includes a feedthrough assembly having at least one terminal conductor at least partially passing through the encasement aperture. According to various embodiments, the feedthrough assembly is adapted to connect a battery cell or a capacitor to the main circuit board.

In one embodiment, a method for manufacturing an encasement for a component of an implantable medical device having a main circuit board is provided. The method includes forming an encasement aperture on a lateral side of the encasement. The lateral side of the encasement is adapted to be placed substantially parallel to a surface of the main circuit board. A feedthrough assembly is connected through the encasement aperture. The feedthrough assembly includes at least one terminal conductor at least partially passing through the encasement aperture. According to various embodiments, the location of the aperture provides for connecting the terminal conductor from a battery cell or capacitor to the main circuit board without bending the terminal conductor.

This summary is an overview of some of the teachings of the present application and is not intended to be an exclusive or exhaustive treatment of the present subject matter. Further details about the present subject matter are found in the detailed description. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter provides encasements for components of implantable medical devices and methods for their manufacture. An encasement for a component of an implantable medical device having a main circuit board includes an encasement aperture on a lateral side of the encasement. The lateral side of the encasement is adapted to be placed substantially parallel to a surface of the main circuit board. The encasement further includes a feedthrough assembly having at least one terminal conductor at least partially passing through the encasement aperture. According to various embodiments, the feedthrough assembly is adapted to connect a battery cell or a capacitor to the main circuit board.

Patients prone to irregular heart rhythms sometimes have miniature heart devices, such as defibrillators and cardioverters, implanted in their bodies. These devices detect onset of abnormal heart rhythms and apply corrective electrical therapy to the heart. The defibrillator or cardioverter includes a set of electrical leads, which extend from a device housing into the heart. Components can have their own housings or encasements, and require apertures in the encasement with a feedthrough conductor or interconnect protruding from the aperture to connect to a main circuit board of the device.

Figure 1A:
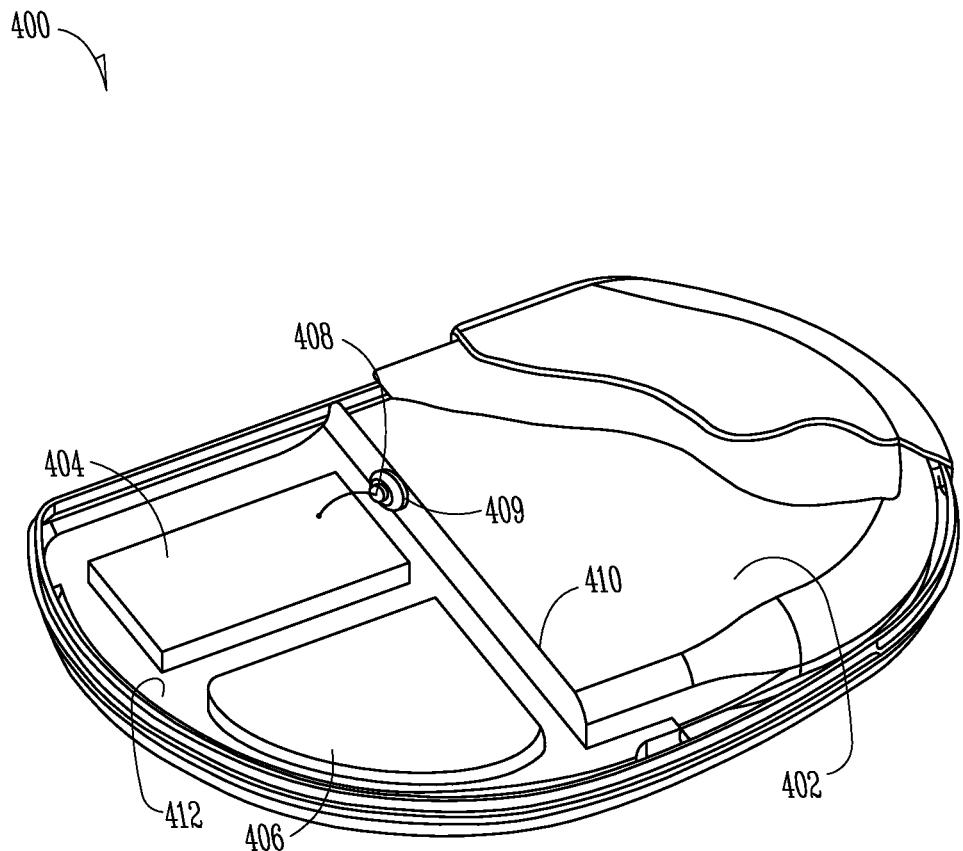
FIG. 1A illustrates an example an implantable medical device.

Interconnections from components such as battery cells or capacitors to the main circuit board (or hybrid board) of the implantable medical device can be difficult to make considering different planes of attachment. The typical component connector comes out of the component encasement on a radial axis of the encasement, which makes the connector parallel to the board. Thus, the connector or the board must be bent at a 90 degree angle to make the connection. FIG. 1A illustrates an example of an encasement for a component of an implantable medical device.

In FIG. 1A, an example of a generic IMD 400 is illustrated. In this example, IMD 400 includes a power source section 402, an electronics section 404, a capacitor section 406, and one or more feedthrough assemblies 408. The "IMD" will typically include, among other things, cardiac function management (referred to as "CFM") systems such as pacemakers, cardioverters/defibrillators, paces/defibrillators, biventricular or other multi-site resynchronization or coordination devices such as cardiac resynchronization therapy (referred to as "CRT") devices, or drug delivery systems.

Power source section 402 may include, but is not limited to, an electrochemical cell, an electrolytic or other capacitor, or a battery. In one example, power source section 402 comprises a battery having an anode or a cathode terminal and is enclosed by an encasement 410, such as a can or other container. In the example, encasement 410 includes at least one encasement aperture 409 into which the one or more feedthrough assemblies 408 are mounted. As discussed, feedthrough assembly 408 penetrates the otherwise sealed encasement 410, such as to provide electrical access to or from one or more electrical components (e.g., an anode or a cathode terminal) enclosed therewithin.

Notably, FIG. 1A illustrates one example of various sections and assemblies of an IMD 400. Power source section 402, electronics section 404, capacitor section 406, and the one or more feedthrough assemblies 408 are illustrated separately for conceptual clarity; however, such sections and assemblies may be further separated or need not be separately embodied.

Figure 1B:
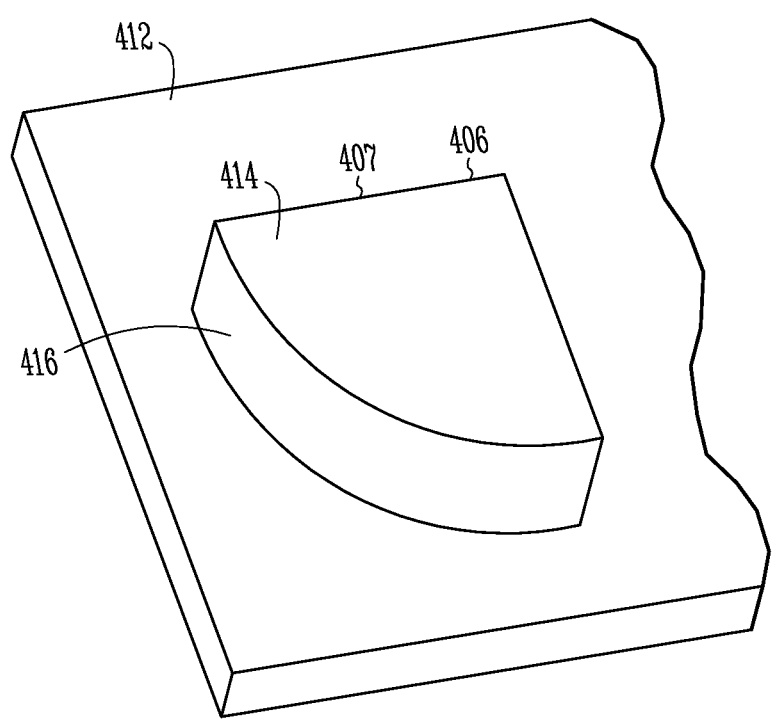
FIG. 1B illustrates an example of an encasement for a component of an implantable medical device.

FIG. 1B illustrates an example of an encasement for a component of an implantable medical device. The component depicted is capacitor section 406 from FIG. 1A, shown as a representative example. The section has an encasement 407 placed relative to a circuit board 412 of an IMD. The encasement 407 has a radial side 416 that is perpendicular to the circuit board 412, and a lateral side 414 that is parallel to the circuit board 412. The lateral side 414 and radial side 416 are perpendicular to each other. The lateral side 414 is the largest flat side (or major surface) of the encasement, and is referred to herein as the z-axis side.

Figure 1C:
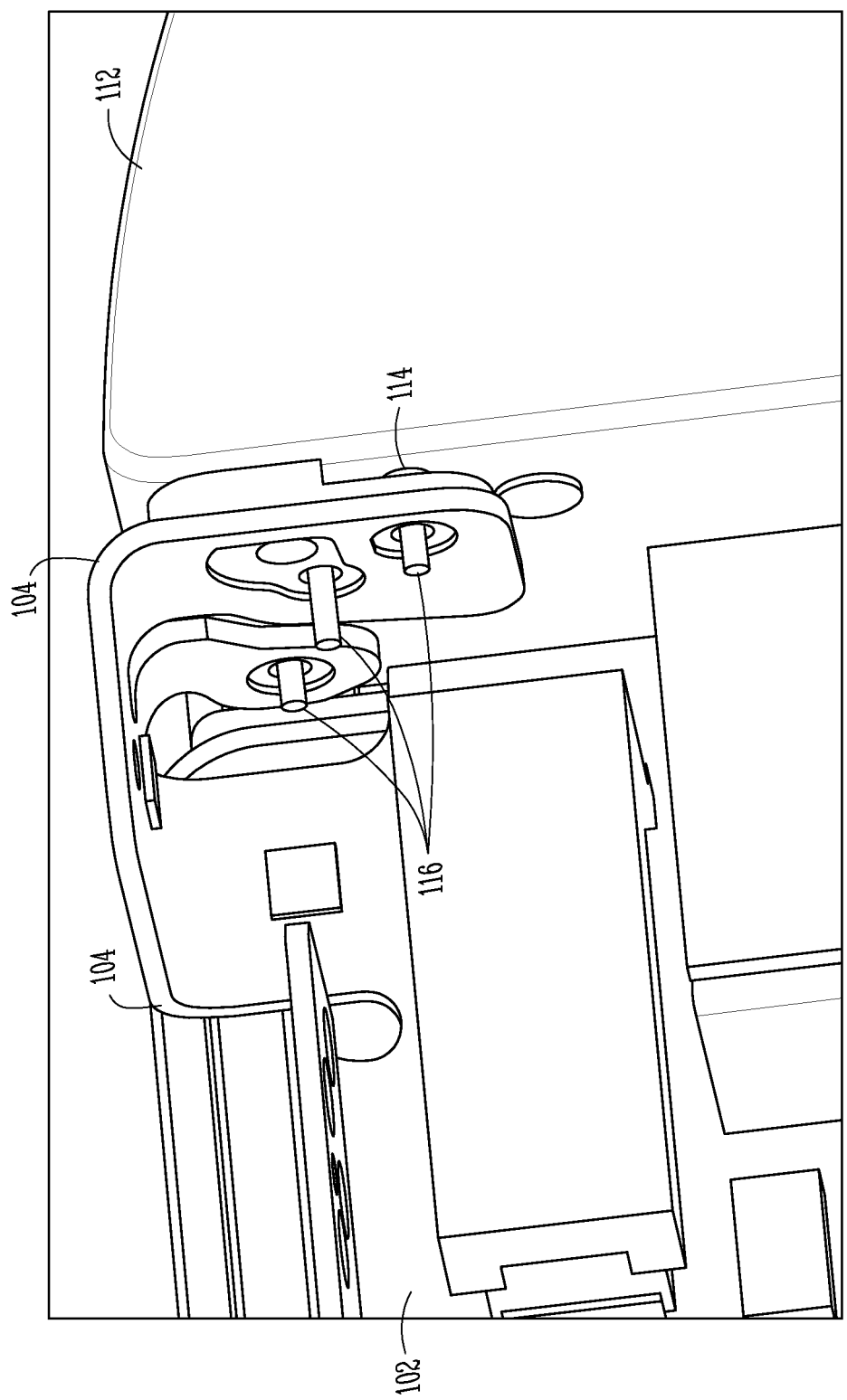
FIG. 1C illustrates an example of a feedthrough interconnection on a radial surface of an encasement of a component of an implantable medical device.

FIG. 1C illustrates an example of a feedthrough interconnection on a radial surface of an encasement of a component of an implantable medical device. Traditional component encasements 112 included feedthrough apertures 114 on a radial side of the encasement. The interconnect conductors 116 protrude through the apertures 114 to mate with the main circuit board 102. However, the location of the feedthrough apertures 114 require bending of the circuit board 102 at bends 104 to properly line up with the conductors 116.

Figure 1D:
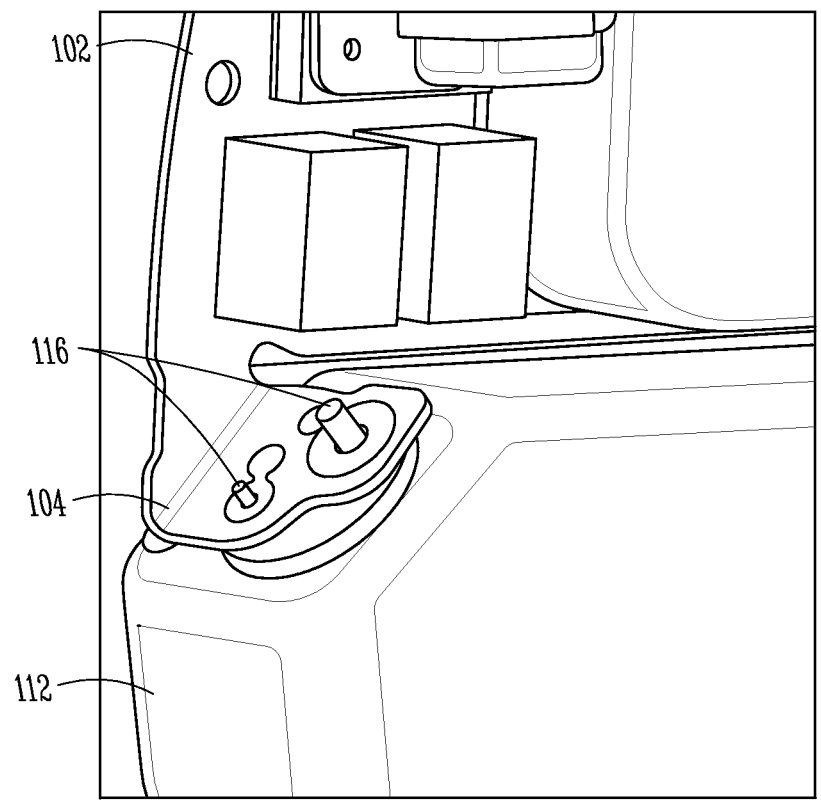
FIG. 1D illustrates another example of a feedthrough interconnection on a radial surface of an encasement of a component of an implantable medical device.

FIG. 1D illustrates another example of a feedthrough interconnection on a radial surface of an encasement of a component of an implantable medical device. Complicated folding of the circuit board 102 is done at bends 104 to mate up with interconnect conductors 116 of the component 112. The interconnect space can take up significant volume in the IMD. Bending wires and boards is a burden for manufacturing and may cause damage to the device or component connections.

Figure 2A:
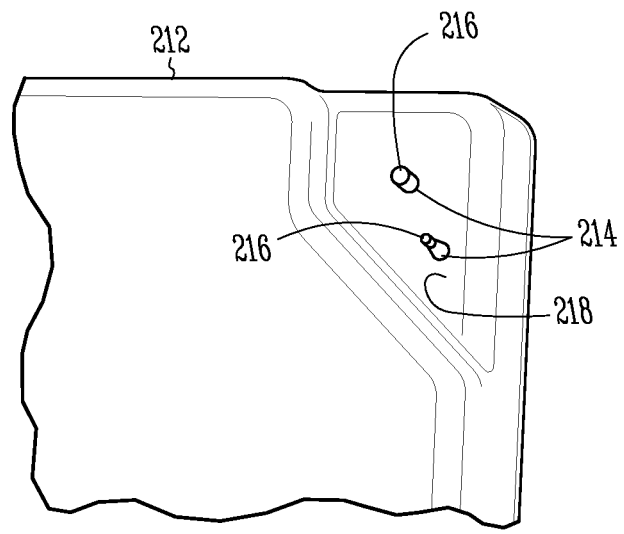
FIG. 2A illustrates a feedthrough interconnection on a lateral side surface of an encasement, according to an embodiment of the present subject matter.
Figure 2B:
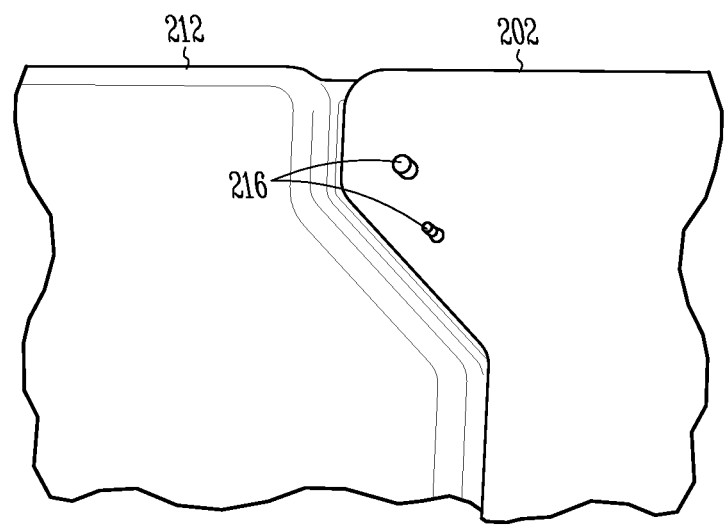
FIG. 2B illustrates a feedthrough interconnection for an implantable component, the feedthrough interconnection on a lateral side surface of an encasement, according to an embodiment of the present subject matter.

FIGS. 2A-2B illustrate feedthrough interconnections for an implantable component, the feedthrough interconnection on a lateral side surface of an encasement, according to an embodiment of the present subject matter. A feedthrough interconnect system is provided that is side mounted on a lateral side of the component encasement. Having a laterally side mounted feedthrough rotates the feedthrough perpendicular to the previous radial mounted feedthroughs. A component encasement 212 has apertures 214 on the lateral face of the encasement 218. The side mount system provides better interconnections, as the conductor 216 protruding from the aperture 214 in the encasement 212 can be connected to the main circuit board 202 without additional flex circuits or wire bends.

An encasement for a component of an implantable medical device having a main circuit board includes an encasement aperture on a lateral side of the encasement. The lateral side of the encasement is adapted to be placed substantially parallel to a surface of the main circuit board. The encasement further includes a feedthrough assembly having at least one terminal conductor at least partially passing through the encasement aperture. According to various embodiments, the feedthrough assembly is adapted to connect a battery cell or a capacitor to the main circuit board without bending the terminal conductor. The lateral side of the encasement is substantially perpendicular to a radial side of the encasement, in an embodiment. An insulator can be disposed within at least a portion of the encasement aperture and surrounding at least a portion of the terminal conductor extending through the encasement aperture. In various embodiments, a ferrule is disposed within at least a portion of the encasement aperture and surrounding at least a portion of the insulator, and the terminal conductor comprises a material having a coefficient of thermal expansion substantially the same as a coefficient of thermal expansion of the insulator. The main circuit board includes a hybrid circuit or flex circuit, in various embodiments. The present subject matter can be used with a variety of implantable medical device, including but not limited to pacemakers, defibrillators and neural stimulators.

Figure 3:
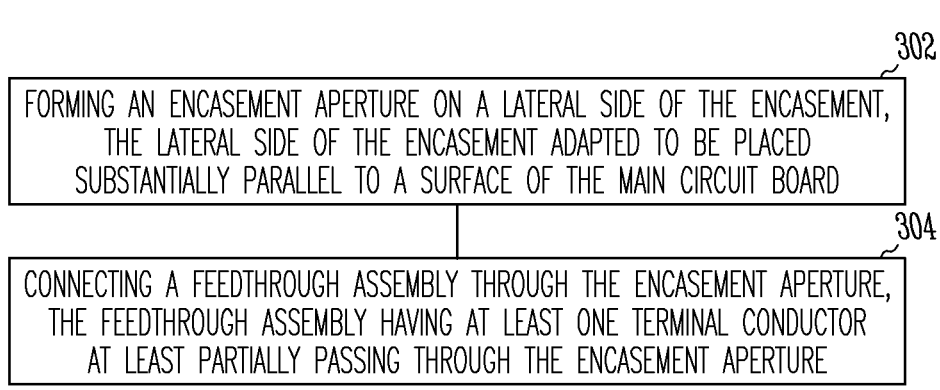
FIG. 3 is a flow chart illustrating an embodiment of a method for manufacturing an encasement for a component of an implantable medical device.

FIG. 3 is a flow chart illustrating an embodiment of a method for manufacturing an encasement for a component of an implantable medical device. The method includes forming an encasement aperture on a lateral side of the encasement, at 302. The lateral side of the encasement is adapted to be placed substantially parallel to a surface of the main circuit board. At 304, a feedthrough assembly is connected through the encasement aperture. The feedthrough assembly includes at least one terminal conductor at least partially passing through the encasement aperture. According to various embodiments, the location of the aperture allows the terminal conductor from a battery cell or capacitor to be connected to the main circuit board without bending the terminal conductor. In some embodiments, for example, the battery cell is adapted to power the IMD, and the capacitor is adapted to store charge for delivery of electrical therapy by the IMD, in various embodiments. Forming an encasement aperture on a lateral side of the encasement includes forming the aperture through a surface of the encasement substantially perpendicular to a radial side of the encasement, in an embodiment. The encasement is manufactured such that the feedthrough assembly is connected without bending the terminal conductor, in various embodiments.

The present subject matter provides for simplified connections between sealed components and a main IMD circuit board. Advantages include decreased overall device size, yield enhancements due to ease of assembly, reduced part counts, and elimination of bending that can compromise structural integrity of circuits and conductors. In addition, the present subject matter provides for fixtureless assembly with z-axis assembly options, resulting in reduced development time and associated benefits.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An encasement for a component of an implantable medical device having a main circuit board exterior to the encasement, the encasement comprising:
    a first portion of the encasement having a major surface with a first lateral face;
    a second portion of the encasement having the major surface with a second lateral face, the second lateral face parallel to and recessed from the first lateral face thickness;
    an encasement aperture on the second lateral face, the second lateral face adapted to be placed substantially parallel to a surface of the main circuit board; and
    a feedthrough assembly having at least one terminal conductor at least partially passing through the encasement aperture and at least partially passing through the main circuit board exterior to the second portion of the encasement.

2. The encasement of claim 1, wherein the feedthrough assembly is adapted to connect a battery cell to the main circuit board without bending the terminal conductor.

3. The encasement of claim 1, wherein the feedthrough assembly is adapted to connect a capacitor to the main circuit board without bending the terminal conductor.

4. The encasement of claim 1, wherein the second lateral face of the encasement is substantially perpendicular to a radial side of the encasement.

5. The encasement of claim 1, comprising an insulator disposed within at least a portion of the encasement aperture and surrounding at least a portion of the terminal conductor extending through the encasement aperture.

6. The encasement of claim 5, comprising a ferrule disposed within at least a portion of the encasement aperture and surrounding at least a portion of the insulator.

7. The encasement of claim 5, wherein the terminal conductor comprises a material having a coefficient of thermal expansion substantially the same as a coefficient of thermal expansion of the insulator.

8. The encasement of claim 1, wherein the main circuit board includes a hybrid circuit.

9. The encasement of claim 1, wherein the implantable medical device includes a pacemaker.

10. The encasement of claim 1, wherein the implantable medical device includes a defibrillator.

11. The encasement of claim 1, wherein the implantable medical device includes a neural stimulator.

12. The encasement of claim 1, wherein the feedthrough assembly is adapted to connect to the main circuit board without bending the terminal conductor.

13. The encasement of claim 9, comprising an insulator disposed within at least a portion of the encasement aperture and surrounding at least a portion of the terminal conductor extending through the encasement aperture.

14. The encasement of claim 13, wherein the terminal conductor comprises a material having a coefficient of thermal expansion substantially the same as a coefficient of thermal expansion of the insulator.

15. The encasement of claim 10, comprising an insulator disposed within at least a portion of the encasement aperture and surrounding at least a portion of the terminal conductor extending through the encasement aperture.

16. The encasement of claim 15, comprising a ferrule disposed within at least a portion of the encasement aperture and surrounding at least a portion of the insulator.

17. The encasement of claim 15, wherein the terminal conductor comprises a material having a coefficient of thermal expansion substantially the same as a coefficient of thermal expansion of the insulator.

18. The encasement of claim 11, comprising an insulator disposed within at least a portion of the encasement aperture and surrounding at least a portion of the terminal conductor extending through the encasement aperture.

19. The encasement of claim 18, comprising a ferrule disposed within at least a portion of the encasement aperture and surrounding at least a portion of the insulator.

20. The encasement of claim 18, wherein the terminal conductor comprises a material having a coefficient of thermal expansion substantially the same as a coefficient of thermal expansion of the insulator.

* * * * *